United States Patent [19]

Holmes

[11] Patent Number: 4,734,504

[45] Date of Patent: Mar. 29, 1988

[54] 1-ALKYLATED DIAZOLIDINONES

[75] Inventor: Richard E. Holmes, Indianapolis, Ind.

[73] Assignee: Eli Lilly and Company, Indianapolis, Ind.

[21] Appl. No.: 862,918

[22] Filed: May 14, 1986

[30] Foreign Application Priority Data

Apr. 28, 1986 [EP] European Pat. Off. ........ 86303174.6

[51] Int. Cl.$^4$ .......................................... C07D 231/08
[52] U.S. Cl. .................................... 548/364; 544/182;
544/238; 544/310; 544/333; 546/279; 548/128;
548/129; 548/130; 548/131; 548/132; 548/136;
548/142; 548/143; 548/144; 548/204; 548/229;
548/236; 548/251; 548/253; 548/255; 548/365
[58] Field of Search ............................... 548/364–365,
548/128, 129, 130, 131, 132, 136, 142, 143, 144,
204, 229, 236, 251, 253, 255; 544/182, 238, 310,
333; 546/279

[56] References Cited

FOREIGN PATENT DOCUMENTS

| 64058 | 5/1968 | German Democratic Rep. ................................. 548/365 |
| 110868 | 1/1975 | German Democratic Rep. ................................. 548/365 |
| 1472052 | 4/1977 | United Kingdom ................ 548/365 |
| 2073740A | 10/1981 | United Kingdom ................ 548/365 |

OTHER PUBLICATIONS

M. Ueda, M. Funayama and Y. Imai, *J. Polymer Science Polym. Chem. Ed.*, 15, pp. 1629–1635, (1977).

M. A. Breger, *Antibiotiki*, 16, pp. 26–27, (1961).

H. Dorn and A. Otto, *Angew. Chem. Int. Ed. Engl.*, 7, pp. 214–215, (1968).

H. Dorn and A. Otto, *Chem. Ber.*, 101, pp. 3287–3301, (1968).

H. Dorn and A. Zubek, *Z. Chem.*, 8, pp. 218–219, (1968).

*Primary Examiner*—Henry R. Jiles
*Assistant Examiner*—Kurt G. Briscoe
*Attorney, Agent, or Firm*—Paul C. Steinhardt; Leroy Whitaker

[57] ABSTRACT

1-Alkylated diazolidinones are intermediates to bicyclic pyrazolidinone antimicrobial compounds.

7 Claims, No Drawings

1-ALKYLATED DIAZOLIDINONES

SUMMARY OF THE INVENTION

The invention is directed to intermediate compounds of the formula

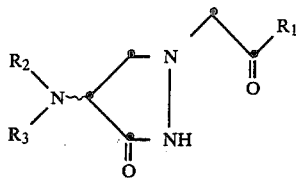

wherein $R_1$, $R_2$, and $R_3$ have the meanings defined below. The instant compounds are intermediates to antimicrobial compounds.

DETAILED DESCRIPTION OF THE INVENTION

I. The Invention in General; Definition of Terms

The present invention embraces compounds of the Formula I:

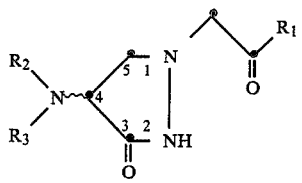

The ring system of the compound of Formula I is a 4-(substituted or unsubstituted amino)-3-oxo-1-(alkylated)diazolidine, referred to below for brevity's sake as a "1-alkylated diazolidinone" or, more simply, "1-alkylated compound". The 1-alkylated diazolidinones are intermediates to bicyclic pyrazolidinone antimicrobial compounds. The numbering system for the diazolidinone ring is denoted in Formula I.

In the above Formula, the undulating line connecting the nitrogen atom to position 4 of the ring system indicates that the stereochemistry at position 4 could be independently in the R or S configuration. Furthermore, the Formula represents compounds of the invention in all of the possible enantiomeric and diastereomeric mixtures.

In the above Formula I:

$R_1$ is $C_1$ to $C_6$ alkyl, $C_1$ to $C_6$ substituted alkyl, perfluoro $C_2$ to $C_4$ alkyl, $C_7$ to $C_{12}$ arylalkyl, $C_7$ to $C_{12}$ substituted arylalkyl, phenyl, substituted phenyl, or a heterocyclic ring; a group of the formula

—$CX_3$ in X is fluoro, chloro, bromo or iodo; or a group of the formula

—S—$R_4$ wherein $R_4$ is $C_1$ to $C_6$ alkyl, $C_1$ to $C_6$ substituted alkyl, phenyl, substituted phenyl, $C_7$ to $C_{12}$ arylalkyl, $C_7$ to $C_{12}$ substituted arylalkyl or a heterocyclic ring;

$R_2$ and $R_3$ are:

(1) each hydrogen;

(2) taken together and form a phthalimido group; or (3) different and are either hydrogen or an amino-protecting group;

or a pharmaceutically-acceptable salt thereof.

In the above Formula I, the term "$C_1$ to $C_6$ alkyl" denotes such radicals as methyl, ethyl, n-propyl, iso-propyl, n-butyl, sec-butyl, tert-butyl, amyl, tert-amyl, hexyl and the like. The preferred "$C_1$ to $C_6$ alkyl" group is methyl.

The term "$C_1$ to $C_6$ substituted alkyl" denotes the above $C_1$ to $C_6$ alkyl groups that are substituted by one or two hydroxy, protected hydroxy, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, 6-hydroxyhexyl, 2-amino(iso-propyl), 2-carbamoyloxyethyl and the like. A preferred group of examples within the above "$C_1$ to $C_6$ substituted alkyl" group includes the substituted methyl group, in other words, a methyl group substituted by the same substituents as the "$C_1$ to $C_6$ substituted alkyl" group. Examples of the substituted methyl group include groups such as hydroxymethyl, protected hydroxymethyl, (e.g., tetrahydropyranyloxymethyl), acetoxymethyl and carbamoyloxymethyl.

The term "$C_1$ to $C_4$ alkoxy" as used herein denotes groups such as methoxy, ethoxy, n-propoxy, isopropoxy, n-butoxy, t-butoxy and like groups. The term "$C_1$ to $C_7$ acyloxy" denotes herein groups such as formyloxy, acetoxy, propionyloxy, butyryloxy, pentanoyloxy, hexanoyloxy, heptanoyloxy, and the like.

Examples of the term "perfluoro $C_2$ to $C_4$ alkyl" include perfluoroethyl, perfluoro n-propyl, perfluoro iso-propyl, perfluoro n-butyl, perfluoro sec-butyl, and the like.

The term "substituted phenyl" specifies a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino).

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(iso-propoxy)phenyl, 4-(t-butoxy)phenyl, 3-ethoxy-4- methoxyphenyl and the like; 3- or 4- trifluoromethylphenyl; a mono- or dicarboxyphenyl or (protected carboxy)phenyl group such as 4-carboxyphenyl or 2,4-di(-protected carboxy)phenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-(protected hydroxy)phenyl, the 2-(protected aminomethyl)phenyl and the 3-(N-(methylsulfonylamino))phenyl groups.

The terms "halo" and "halogen" refer to the fluoro, chloro, bromo or iodo groups.

The term "$C_7$ to $C_{12}$ arylalkyl" denotes a $C_1$ to $C_6$ alkyl group substituted at any position by a phenyl ring. Examples of such a group include phenyl methyl (benzyl), 2-phenylethyl, 3-phenyl-(n-propyl), 4-phenylhexyl, 3-phenyl-(n-amyl), 3-phenyl-(sec-butyl), and the like. A preferred group is the benzyl group.

The term "$C_7$ to $C_{12}$ substituted arylalkyl" denotes a $C_7$ to $C_{12}$ arylalkyl group substituted on the $C_1$ to $C_6$ alkyl portion with one or two groups chosen from hydroxy, protected hydroxy, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or a N-(methylsulfonylamino) group. As before, when either the $C_1$ to $C_6$ alkyl portion or the phenyl portion or both are disubstituted, the substituents can be the same or different.

Examples of the term "$C_7$ to $C_{12}$ substituted arylalkyl" include groups such as 2-phenyl-1-nitroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomephenyl)-3-(aminomethyl)(n-pentyl), and the like.

The term "pharmaceutically-acceptable salt" encompasses those salts that form with the carboxylate anions and includes salts formed with the organic and inorganic cations discussed above. The counter-ions are chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)ammonium, phenylethylbenzylammonium, dibenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine. Also, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used in the specification refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the condition of subsequent reaction(s) on other positions of the 1-alkylated diazolidinones molecule and can be removed at the appropriate point without disrupting the remainder of either the 1-alkylated diazolidinones or the subsequent bicyclic pyrazolidinone products. In particular, it is important not to subject the carboxy-protected 1-alkylated diazolidinones or the bicyclic pyrazolidinones to strong nucleophilic bases or reductive conditions employing highly activated metal catalysts such as Raney nickel. (Such harsh removal conditions are also to be avoided when removing amino-protecting groups and hydroxy-protecting groups, discussed below.) A preferred carboxylic acid protecting group is the allyl group. Similar carboxy-protecting groups used in the cephalosporin, penicillin and peptide arts can also be used to protect carboxy group substituents of the bicyclic pyrazolidinones. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, $\beta$-methoxyethoxymethyl, methylthiomethyl, t-butyl, t-amyl, trityl, 4- methoxytrityl, 4,4'-dimethoxytrityl, 4,4',4"-trimethoxytrityl, benzyl, allyl, trimethylsilyl, (t-butyl)dimethylsilyl, and the 2,2,2-trichloroethoxycarbonyl groups.

The species of hydroxy-protecting groups is not critical so long as the derivatized hydroxyl group is stable to the conditions of subsequent reaction(s) and can be removed at the appropriate point without disrupting the remainder of either the 1-alkylated diazolidinone or the subsequent bicyclic pyrazolidinone products.

Further examples of hydroxy-protecting groups are described by C. B. Reese and E. Haslam, "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. Some preferred hydroxy-protecting groups are the trityl group and the tetrahydropyranyl group. The related term "protected hydroxy" denotes a hydroxy group bonded to one of the above hydroxy-protecting groups.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl 2-(methylsulfonyl) ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilyl methyl)prop-1-enyloxycarbonyl, 5-benzisoxalylmethoxycarbonyl, 4-acetoxybenzyloxycarbonyl, 2,2,2-trichloroethoxycarbonyl, 2-ehtynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the 1-alkylated diazolidinone molecule and can be removed at the appropriate point without disrupting the remainder of either the 1-alkylated diazolidinone or the subsequent bicyclic pyrazolidinone products. Preferred amino-protecting groups are the allyloxycarbonyl, the t-butoxycarbonyl, and the trityl groups. Similar amino-protecting groups used in the cephalosporin, penicillin and peptide art are also embraced by the above term. Further examples of groups referred to by the above term are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

The term "non-toxic, metabolically-labile ester-forming group" refers to those biologically active ester forms which induce increased blood levels and prolong the efficacy of the corresponding non-esterified forms of the compounds. Such ester groups include the lower alkoxymethyl groups, for example, methoxymethyl, $\alpha$-($C_1$ to $C_4$)alkoxyethyl groups, for example methoxyethyl, ethoxyethyl, propoxyethyl, iso-propoxyethyl, and the like; the 2-oxo-1,3-dioxolen-4-ylmethyl groups, such as 5-methyl-2-oxo-,1,3-dioxolen-4-ylmethyl, 5-phenyl-2-oxo-,1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, $\alpha$-acetoxymethyl, and the like; the ethoxycarbonyl-1-methyl group; the $\alpha$-acyloxy-$\alpha$-substituted methyl groups, for example $\alpha$-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred.

Furthermore, the above optionally substituted five-membered or six-membered rings can optionally be fused to a aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-9 pyridazinyl and purinyl, as well as benzo-fused derivatives, for example benzoxazolyl, benzthiazolyl, benzimidazolyl and indolyl.

A preferred group of examples of the above heterocyclic rings, when $R_1$ is a heterocyclic group, are 5-membered ring systems containing a sulfur or oxygen atom and one to three nitrogen atoms. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl;

1,2,3-triazol-5-yl, 1,2,4-triazol-5-yl, and tetrazolyl, preferably 1H-tetrazol-5-yl. A preferred group of examples of benzo-fused derivatives are, in particular, benzoxazol-2-yl, benzthiazol-2-yl and benzimidazol-2-yl.

Further specific examples of the above heterocyclic ring systems are 6-membered ring systems containing one to three nitrogen atoms. Such examples include pyridyl, such as pyrid-2-yl, pyrid-3-yl and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides, and the pyridyl, pyrimid-2-yl, pyrimid-4-yl, pyridazinyl and the 1,3,4-triazin-2-yl radicals, are a preferred group.

The substituents for the optionally substituted heterocyclic ring systems, and further examples of the 5- and 6- membered ring systems discussed above, are found in W. Dürckheimer et al., U.S. Pat. No. 4,278,793, issued July 14, 1981, columns 9 through 21 and columns 33 through 188, herein incorporated by reference. (In columns 33 through 188, examples of the term "heterocyclic ring" are included in the heterocyclic thiomethyl groups listed under heading "A".)

A particularly preferred group of examples of the term "heterocyclic ring" is 1,3-thiazol-2-yl, 4-(protected carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-(protected carboxy)-4-methyl-1,3,4-triazol-5-yl, 1,3-oxazol-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiadazol-5-yl, 2-(methylthio)-1,3,4-thiadiazol-5-yl, 2-(protected amino)-1,3,4-thiadiazol-5-yl, 1H-tetrazol-5-yl, 1-methyl-1H-tetrazol -5-yl, 1-(1-(dimethylamino)eth-2-yl)-1H-tetrazol-5-yl, 1-(protected carboxymethyl)-1H-tetrazol-5-yl, 1-(methylsulfonic acid)-1H-tetrazol-5-yl, 1-(methylsulfonic acid)-1H-tetrazol-5-yl sodium salt, 2-methyl-1H-tetrazol -5-yl, 1,2,3-triazol-5-yl, 1-methyl-1,2,3triazol-5-yl, 2-methyl-1,2,3-triazol-5-yl, 4-methyl -1,2,3-triazol-5-yl, pyrid-2-yl N-oxide, 6-methoxy-2-(N-oxide)-pyridaz-3-yl, 6-hydroxypyridaz-3-yl, 1-methylpyrid -2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-as-triazin-3-yl, 2,5-dihydro-5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin 3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro 1,5-oxo-2,6-dimethyl-as-triazin-3-yl, tetrazolo[1,5-b]-pyridazin-6-yl and 8-aminotetrazolo[15-]pyridazin-6-yl.

A most preferred group of examples of the term "heterocyclic ring" is 4-(protected carboxymethyl)-5-methyl-1,3-thiazol-2-yl, 1,3,4-triazol-5-yl, 2-methyl-1,3,4-triazol-5-yl, 1H-tetrazol -5-yl, 1methyl-1H-tetrazol-5-yl, 1-(1-dimethylamino)eth-2-yl)-1H-tetrazol-5yl, 1(protected carboxymethyl)-1H-tetrazol-5-yl, 1-(methylsulfonic acid)-1H-tetrazol-5-yl, 1-(methylsulfonic acid) -1H-tetrazol-5-yl sodium salt, 1,2,3-triazol-5-yl, 1,4,5,6-tetrahydro-5,6dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as triazin-3-yl sodium salt, 2,5-dihydro-5-oxo-6-hydroxy-2-methyl-as-triazin-3-yl, tetrazolo[1,5-b]-pyridazin-6-yl, and 8-aminotetrazolo[1,5-b]pyridazin-6-yl.

In the above Formula I, when $R_1$ is a group of the formula $$-S-R_4$$

wherein $R_4$ is a heterocyclic group, examples of such groups are 1,3-thiazol-2-ylthio, 4-(protected carboxymethyl)-5-methyl-1,3-thiazol-2-ylthio, 1,2,4thiadiazol-5-ylthio, 3-methyl-1,2,4-thiadiazol-5-ylthio, 1,3,4-triazol-5-ylthio, 2-methyl-1,3,4-triazol-5-ylthio, 2-hydroxy-1,3,4-triazol-5-ylthio, 2-(protected carboxy) 4-methyl-1,3,4-triazol-5-ylthio, 1,3-oxazol-2-ylthio, 1,3,4-oxadiazol-5-ylthio, 2-methyl-1,3,4-oxadiazol-5-ylthio, 2-(hydroxymethyl)-1,3,4-oxadiazol-5-ylthio, 1,2,4-oxadiazol-5-ylthio, 1,2,4-oxadiazol-5-ylthio, 1,3,4-thiadiazol-5-ylthio, 2-methyl-1,3,4-thiadiazol-5ylthio, 2-(methylthio)-1,3,4-thiadiazol-5-ylthio 2-(protected amino)-1,3,4-thiadiazol-5-ylthio, 1H-tetrazol-5-ylthio, 1-methyl-1H-tetrazol-5-ylthio, 1-(1(dimethylamino)eth-2-ylthio)-1H-tetrazol-5-ylthio, 1-(protected carboxymethyl)-1H-tetrazol-5-ylthio, 1-(methylsulfonic acid)-1H-tetrazol-5-ylthio, 1-(methylsulfonic acid)-1H-tetrazol-5-ylthio sodium salt, 2-methyl-1H-tetrazol-5-ylthio, 1,2,3-triazol5-ylthio, 1-methyl-1,2,3-triazol-5-ylthio, 2-methyl-1,2,3-triazol-5-ylthio, 4-methyl-1,2,3-triazol-5-ylthio, pyrid-2-ylthio N-oxide, 6-methoxy-2-(N-oxide)-pyridaz3-ylthio, 6-hydroxypyridaz-3-ylthio, 1-methylpyrid-2-ylthio, 1-methylpyrid-4-ylthio, 2-hydroxypyrimid-4-ylthio, 1,4,5,6-tetrahydro-5,6-dioxo-4-methyl-as-triazin-3-ylthio, 1,4,5,6-tetrahydro-4-(2-formylmethyl)-5,6-dioxo-as-triazin-3-ylthio, 2,5-dihydro-5-oxo-6-hydroxy-as-triazin-3-ylthio, 2,5-dihydro-5-oxo-6-hydroxy-as-triazin-3-ylthio sodium salt, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, 2,5-dihydro-5-oxo-6-methoxy-2-methyl-as-triazin-3-ylthio, 2,5-dihydro-5-oxo-as-triazin-3-ylthio, 2,5-dihydro-5-oxo-2-methyl-as-triazin-3-ylthio, 2,5-dihydro-5-oxo-2,6-dimethyl-as-triazin-3-ylthio, tetrazolo[1,5-b]pyridazin-6-ylthio and 8-aminotetrazolo[1,5-b]pyridazin-6-ylthio; and the like.

Examples of the above group when $R_4$ is other than a heterocyclic group include $C_1$ to $C_6$ alkylthio groups such as methylthio, ethylthio, (sec-butyl)thio, (t-amyl)thio and (n-hexyl)thio, $C_7$ to $C_{12}$ phenylalkylthio groups such as 2-phenylpropylthio, benzylthio, 1-phenyl(n-amyl)thio and 4-phenyl(n-butyl)thio; $C_1$ to $C_6$ substituted alkylthio groups such as cyanomethylthio, 2-hydroxyethylthio, 2-nitropropylthio, 2-carbamoyl(secbutyl)thio, 4-carboxyamylthio, 6-carbamoyloxyhexylthio, 2-methoxyethylthio, isopropoxy(t-butyl)thio, 2-(protected amino)ethylthio, 2,5-dihydroxyamylthio, and 4-acetoxy-6-fluorohexylthio; $C_7$ to $C_{12}$ substituted phenylalkylthio groups such as 3-(3,4-diiodophenyl)-propylthio, 1-(3-chloro-4-fluorophenyl)ethylthio, 6-(4-cyanophenyl)hexylthio, 2-phenyl-2-hydroxyethylthio, 5-phenyl-2-hydroxyamylthio, 2-(3-nitrophenyl)-3-ethoxypropylthio, 5,6-dihydroxy-2-(4-ethyl-2-(hydroxyphenyl) hexylthio and 5-carbamoyl-3-nitro-2-(2,4-dimethoxyphenyl)amylthio; phenylthio, and (substituted phenyl)thio groups.

Examples of the (substituted phenyl)thio groups represented by $R_4$ include groups such as 4-chlorophenylthio, 2,6-dichlorophenylthio, 2,5-dichlorophenylthio, 3,4-dichlorophenylthio, 3-chlorophenylthio, 3-bromophenylthio, 4-bromophenylthio, 3,4 dibromophenylthio, 3-chloro-4-fluorophenylthio, 2-fluorophenylthio, 4-hydroxyphenylthio, 3-hydroxyphenylthio, 2,4-dihydroxyphenylthio, 3- or 4-nitrophenylthio, 4-cyanophenylthio, 4-methylphenylthio, 2,4-dimethylphenylthio, 2-methylphenylthio, 4-(iso-propyl)phenylthio, 4-ethylphenylthio, 3-(n-propyl)phenylthio, 2,6-dimethoxyphenylthio, 4-methoxyphenylthio, 3-ethoxyphenylthio, 4-(iso-propoxy)phenylthio, 4-(t-butoxy)phenylthio, 3-ethoxy-4-methoxyphenylthio, a 3- or 4-(trifluoromethyl)phenylthio, 4-(protected carboxy)phenylthio, 2,4-di(protected carboxy)phenylthio, 3-(protected hydroxymethyl)phenylthio, 3,4-di(hydroxymethyl)phenylthio, 2,4-di(protected aminomethyl)phenylthio, 3-(N-(methylsulfonylamino))phenylthio, 3-methyl-4-hydroxyphenylthio, 3-chloro-4-hydroxyphenylthio, 2-methoxy-4-bromophenylthio, 4-ethyl-2-hydroxyphenylthio, 3-hydroxy-4-nitrophenylthio, and 2-hydroxy-4-chlorophenylthio.

A preferred group of examples of the group

—S—R$_4$ include: 4-(protected carboxymethyl)-5-methyl-1,3-thiazol -2-ylthio, 1,3,4-triazol-5-ylthio, 2-1,3,4-triazol-5-ylthio, 1H-tetrazol-5-ylthio, 1 methyl-1H-tetrazol-5-ylthio, 1-(1-(dimethylamino)eth-2-ylthio)-1H-tetrazol-5ylthio, 1-(protected carboxymethyl)-1H-tetrazol-5-ylthio, 1-(methylsulfonic acid)1 H-tetrazol-5-ylthio, 1-(methylsulfonic acid)-1H-tetrazol-5-ylthio sodium salt, 1,2,3-triazol-5-ylthio, 1,4,5,6-tetrahydro-5,6-dioxo-4-methyl-as-triazin-3-ylthio, 1,4,5,6-tetrahydro-4-(formylmethyl)-5,6-dioxo- as-triazin-3-ylthio, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, tetrazolo[1,5-b]pyridazin-6-ylthio, 8-aminotetrazolo[1,5-b]pyridazin-6-ylthio, methylthio and phenylthio.

A preferred group of compounds of Formula I occurs when either R$_2$ or R$_3$ is hydrogen and the other is an amino-protecting group, in other words, the amino-protected 1-alkylated diazolidinone compounds. A preferred group of the amino-protected 1-alkylated diazolidinone compounds has R$_1$ as a heterocyclic group, and a further preferred group has R$_1$ as a 2-thienyl group. Compounds of note within this latter group of 2-thienyl compounds are when either R$_2$ or R$_3$ is hydrogen and the other is a t-butoxycarbonyl group.

Another preferred group of compounds are the 4-(S) 1-alkylated diazolidinones of the formula

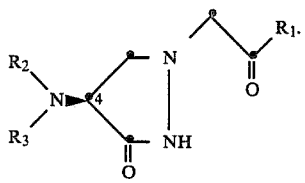

A preferred group of 4-(S) compounds are the amino-protected compounds, wherein either R$_2$ or R$_3$ is hydrogen and the other is an amino-protecting group.

II. Synthesis of the Compounds of Formula I and the Requisite Starting Materials The synthesis of the 1-alkylated diazolidinone compounds of Formula I is set forth below in Scheme I.

Scheme 1

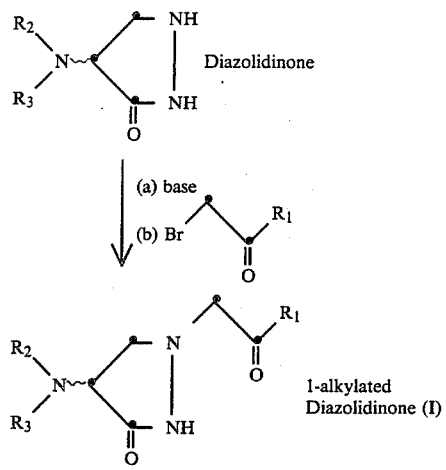

In the above Scheme R$_1$ is the same as for Formula I, while R$_2$ and R$_3$ are the same except that they are not simultaneously hydrogen. Furthermore, it is preferred that any hydroxy, amino, or carboxy groups associated with R$_1$ be in the protected form.

The alkylation of the C$_1$ nitrogen of the diazolidinone with an acetyl fragment that bears the R$_2$ substituent is a two step sequence. The first step of the alkylation is the deprotonation of the diazolidinone with a base chosen from sodium hydride, potassium t-butoxide, and the like. The diazolidinone and the base are preferably combined in a 1:1 molar ratio, but an excess of the diazolidinone is permissible.

The deprotonation step, as well as the subsequent alkylation step, is carried out in polar, aprotic solvents such as dimethylformamide, hexamethylphosphoramide, dimethylsulfoxide or dimethylacetamide. Dimethylformamide is the preferred solvent. When sodium hydride is the base, the reaction is stirred for between 1 to about 1.5 hours (to allow dissolution) then the alkylating agent is added. With the other bases, it is preferred to add the alkylating reagent within a few minutes after the addition of base. The deprotonation reaction mixture is stirred from between 0° C. to about room temperature, with 0° C. being the preferred temperature.

The deprotonated diazolidinone and the bromoacetyl or chloroacetyl alkylating reagent are combined in approximately a 1:1 molar ratio, although an excess of either reagent is permissable. The solvents for the alkylation step are the same as for the deprotonation step, and again dimethylformamide is the preferred solvent. The alkylation is generally complete after about 3 to about 24 hours and is stirred from about 0° C. to about room temperature.

The progress of the alkylation reaction is monitored by conventional chromatographic techniques (such as thin layer chromatography or analytical-scale high pressure liquid chromatography) or spectroscopic techniques (such as infrared spectrometry or nuclear magnetic resonance spectroscopy). Spectroscopic and chromatographic techniques may also be combined to monitor the progress of the reaction. When the monitoring technique(s) demonstrates that the reaction is substantially complete, the products from the above reaction is isolated by conventional methods.

The stereochemistry at $C_4$ of the 4-(S) 1-alkylated diazolidinone product (Formula I) of the reaction sequence in Scheme 1 is determined by the stereochemistry at $C_4$ of the diazolidinone starting material. Thus, a 4-(S) diazolidinone will yield a 4-(S) 1-alkylated diazolidinone product.

The 1-alkylated compounds of Formula I are intermediates to bicyclic pyrazolidinone antimicrobial compounds. The synthetic steps from the compounds of Formula I to the precursors to the antimicrobial compounds is set forth below in Scheme 2.

Scheme 2

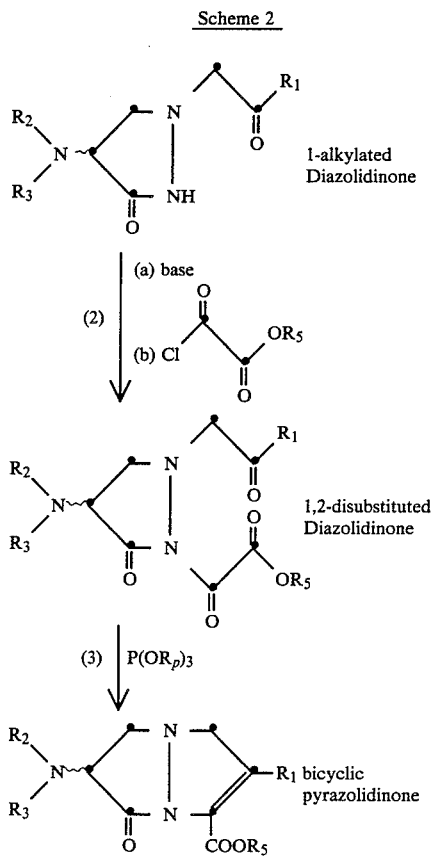

$R_1$, $R_2$ and $R_3$ have the same meaning in Scheme 2 as they do in Scheme 1. $R_5$ is a carboxy-protecting group or a non-toxic, metabolically-labile, ester-forming group. $R_p$ is $C_1$ to $C_6$ alkyl or phenyl.

The 1-alkylated diazolidinone (from Scheme 1) is acylated to yield the 1,2-disubstituted diazolidinone. The acylation reaction is depicted in the above Scheme as Reaction 2. The first step of Reaction 2 is a deprotonation reaction and the second step is the acylation of the resultant anion. The deprotonation step is preferably carried out with di(isopropyl)ethylamine present in an equimolar amount with the 1-alkylated diazolidinone reactant, although either reactant may be present in excess. The deprotonation reactants are combined in any of the chlorinated hydrocarbon solvents, although dichloromethane is preferred. The mixture is stirred from between about 0° C. to about 25° C., with a range of between about 0° C. to about 10° C. being preferred.

Within a few minutes after the addition of the base, the oxalate ester acid chloride acylating agent is added to the mixture, usually in an equimolar amount. A slight excess of the oxalate reactant may also be used. The oxalate reactant is generally added in a dropwise fashion over a period of approximately 20 minutes. The solvent for the acylation step is the same as the solvent of the deprotonation step. The temperature for the acylation step is the same as that for the deprotonation step, with approximately 10° C. being preferred. The acylation reaction will be complete after approximately 6 to approximately 48 hours, with the usual time being approximately 24 hours.

In the final reaction in Scheme 2 (Reaction 3) the 1,2-disubstituted diazolidinone is cyclized to a bicyclic pyrazolidinone. A 5 to 10 molar equivalent excess of the phosphite reagent is combined with the diazolidinone reactant in either chloroform, 1,2-dichloroethylane, or an aromatic hydrocarbon solvent. Chloroform is the preferred solvent. The cyclization reaction mixture is heated to a range of about 50° C. to about 120° C. for between about 12 to about 72 hours. Twenty-four hours is a typical reaction time.

The progress of Reactions 2 and 3 in Scheme 2 is monitored by conventional chromatographic techniques (such as thin layer chromatography or analytical-scale high pressure liquid chromatography) or spectroscopic techniques (such as infrared spectrometry or nuclear magnetic resonance spectroscopy). Spectroscopic and chromatographic techniques may also be combined to monitor the progress of the reactions. When the monitoring technique(s) demonstrates that the reactions are substantially complete, the products from the above reactions are isolated by conventional methods.

The stereochemistry at $C_7$ of the bicyclic pyrazolidinone product of the reaction sequence in Scheme 2 is determined by the stereochemistry at $C_4$ of the 1-alkylated diazolidinone starting material. Thus, a 4-(S) 1-alkylated diazolidinone will yield a 7-(S) bicyclic pyrazolidinone product.

The bicyclic pyrazolidinone compounds produced by the reactions in Scheme 2 above are the 7-(protected amino) intermediate compounds (i.e., when either $R_2$ or $R_3$ is an amino-protecting group and the other is hydrogen). Replacing the amino-protecting group of the 7-(protected amino) compounds with an acyl group derived from a $C_1$ to $C_{30}$ carboxylic acid converts them to the bicyclic pyrazolidinone antimicrobial final products. As discussed above, the acyl groups employed are typically those used to achieve the same purpose when bonded to the 6-amino group of a penicilllin or a 7-amino group of a cephalosporin.

The first step for the acylation of a 7-(protected amino) bicyclic pyrazolinone compound ("7-protected amino nucleus") is the removal of the amino-protecting group. For example, the trimethylsilyl protecting group is removed by simple hydrolysis, the t-butoxycarbonyl group is removed by either acidic hydrolysis (with trifluoroacetic acid) or acidolysis (hydrochloric acid in glacial acetic acid), and the allyloxycarbonyl group is removed as a palladium complex. The conditions for the removal of other groups are well known in the cephalosporin and penicillin arts.

Removal of the acid-labile amino-protecting groups usually yields the 7-amino nucleus as a salt. The salt of the nucleus is neutralized by conventional procedures before acylation. For instance, the removal of the t-butoxycarbonyl group with trifluoroacetic acid leaves the trifluoroacetate salt of the resultant 7-amino nucleus. The salt is taken up in tetrahydrofuran and bis(-trimethylsilyl)trifluoroacetamide is added to yield the corresponding (neutralized) 7-amino compound. The neutralized compound can either be isolated then acylated or acylated in situ.

The methods for the acylation of the neutralized 7-amino bicyclic pyrazolidinone with the acyl side chain are similar to the methods for the acylation of 6-aminopenicillanic acid, 7-aminodesacetoxycephalosporanic acid and 7-aminocephalosporanic acid. One method is to simply combine the 7-amino nucleus with an acid chloride or acid bromide in the presence of an acid scavenger. The acid chloride or acid bromide may be formed in situ. Another method is to combine the 7-amino nucleus with the free carboxylic acid form of the side chain (or its acid salt) and a condensing agent. Suitable condensing agents include N,N'-disubstituted carbodiimides such as N,N'-dicyclohexylcarbodiimide, N,N'-diethylcarbodiimide, N,N'-di-(n-propyl)carbodiimide, N,N'-di-(iso-propyl)carbodiimide, N,N'-diallylcarbodiimide, N,N'-bis(p-dimethylaminophenyl)carbodiimide, N-ethyl-N'-(4"-ethylmorpholinyl)carbodiimide and the like. Other suitable carbodiimides are disclosed by Sheehan in U.S. Pat. No. 2,938,892 and by Hofmann et al. in U.S. Pat. No. 3,065,224. Azolides, such as N,N'-carbonyldiimidazole and N,N'-thionyldiimidazol, may also be used as condensing agents. Dehydrating agents such as phosphorus oxychloride, the alkoxyacetylenes and 2-halogenopyridinium salts (such as 2-chloropyridinium methyl iodide, 2-fluoropyridinium methyl iodide, and the like) may be used to couple the free acid or its acid salt with the 7-amino nucleus.

Another acylation method entails first converting the free carboxylic acid form (or the corresponding salt) of the acyl side chain to the active ester derivative which is in turn used to acylate the nucleus. The active ester derivative is formed by esterifying the free acid form with groups such as p-nitrophenol, 2,4-dinitrophenol, trichlorophenol, pentachlorophenol, 2-chloro-4,6-dimethoxytriazene, N-chlorosuccinimide, N-chloro maleic imide, N-chlorophthalimide, 1-hydroxy-1H-benzotriazole or 1-hydroxy-6-chloro-1H-benzotriazole. The active ester derivatives can also be mixed anhydrides, which are formed with groups such as methoxycarbonyl, ethoxycarbonyl, isobutoxycarbonyl, trichloromethylcarbonyl and iso-but-2-ylcarbonyl and the carboxylic acid of the acyl side chain. The mixed anhydrides are synthesized by acylating the carboxylic acid of the acyl side chain.

Alternatively, the 7-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (such as tetrahydrofuran, acetonitrile, and the like). The resultant EEDQ derivative is used in situ to acylate the 7-amino nucleus.

The antimicrobial activity of the bicyclic pyrazolidinones acylated with the appropriate acyl group derived from a $C_1$ to $C_{30}$ carboxylic acid is further enhanced on removal of any remaining amino, hydroxy and/or carboxy protecting groups on the molecule. As discussed above, such removal methods are generally well known in the cephalosporin, penicillin and peptide arts. Once the carboxy groups are deprotected, the non-toxic, metabolically-labile, ester-forming ("oral ester") group(s) may be put in place on the desired carboxy groups at $R_5$. The methods for making the oral ester derivatives are well known in the cephalosporin and penicillin arts.

The antimicrobial bicyclic pyrazolidone compounds and the corresponding intermediates are also disclosed C. J. Barnett, R. E. Holmes, L. N. Jungheim, S. K. Sigmund, and R. J. Ternansky, U.S. patent application Ser. No. 862,906, filed this even date, herein incorporated by reference, which application in turn is a continuation-in-part of L. N. Jungheim and S. K. Sigmund, U.S. Patent Application Ser. No. 729,021, filed Apr. 30, 1985 now abandoned, also herein incorporated by reference.

A $C_4$-racemic mixture of diazolidinone starting materials for the reactions in Scheme 1 are synthesized according to the process depicted below in Scheme 3.

Scheme 3

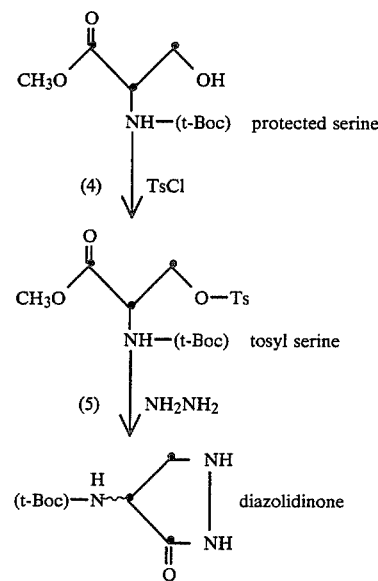

The above Scheme depicts the synthesis of 4-(t-butoxycarbonylamino) diazolidinone starting materials. Diazolidinone starting materials with different amino-protecting groups are obtained by starting with a different protecting group on the protected serine derivative.

The first step in the synthesis of the diazolidinone starting materials, represented by Reaction 4 in the above Scheme, is the tosylation of the hydroxy group of the protected serine derivative. The tosylation is carried out in methylene chloride with p-toluenesulfonyl chloride in the presence of a catalytic amount of 4-dimethylaminopyridine and greater than one equivalent of pyridine. The reaction mixture is stirred at room temperature overnight.

The tosylated serine obtained is cyclized to give the diazolidinone. The cyclization represented by Reaction 5 is carried out by adding the tosyl serine to a solution of 97% hydrazine in methylene chloride under nitrogen. The mixture is then stirred at room temperature for five hours.

The stereospecific synthesis of chiral diazolidinone starting materials is diagramed below in Scheme 4.

Scheme 4

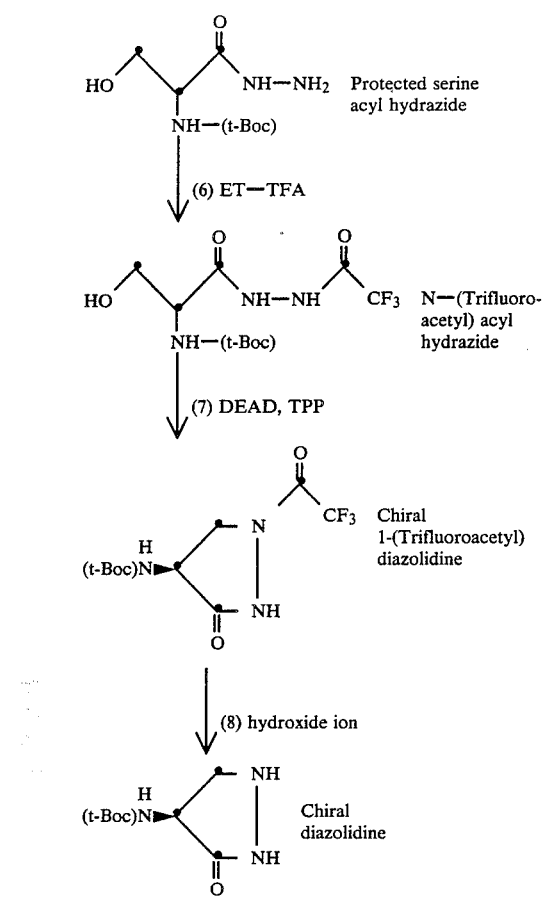

The above Scheme depicts the synthesis of chiral 4-(S)-(t-butoxycarbonylamino) diazolidinone compounds. Diazolidinone compounds with the 4-(R) configuration are synthesized by starting with the protected D-serine acyl hydrazide instead of the L-isomer depicted above. Both 4-(R) or 4-(S) compounds with amino-protecting groups other than t-butoxycarbonyl are synthesized from the corresponding serine enantiomer substituted with an amino-protecting group other than t-butoxycarbonyl.

The protected serine acyl hydrazide precursor of Scheme 4 is synthesized in a procedure analogous to B. Iselin and R. Schwyzer, *Helv. Chim. Acta,* 44, p. 169 (1961). The precursor is then acylated with the trifluoroacetyl moiety, as set forth in Reaction 6 in the Scheme. The hydrazide precursor is acylated with an excess of ethylthio trifluorothioacetate ("ET-TFA") in ethanol. The reaction mixture is stirred at room temperature for 65 hours.

The N-(trifluoroacetyl) acyl hydrazide obtained from Reaction 6 is cyclized with triphenylphosphine ("TPP") and diethyl azodicarboxylate ("DEAD"), as depicted above in Reaction 7.

The stoichiometry of the cyclization of Reaction 7 has the N-(trifluoroacetyl) acyl hydrazide, phosphine and diethyl azodicarboxylate reagent present in at least approximately a 1:1:1 molar ratio. The reaction will proceed in the presence of molar excesses above this ratio of any of the reactants.

The cyclization is initiated by first combining (in any order) the solvent, the N-(trifluoroacetyl) acyl hydrazide and the phosphine, and secondly adding the azodicarboxylate reagent.

The temperature of Reaction 7 is not a critical parameter. The cyclization can be carried out at a temperature from approximately the freezing point to approximately the reflux temperature of the solvent. The preferred temperature is approximately room temperature.

The duration of Reaction 7 can be from approximately five minutes to approximately twenty four hours. The progress of the cyclization can be monitored by standard methods (such as thin layer chromatography, high performance liquid chromatography, etc.) The process is stopped when the monitoring method demonstrates that the reaction is substantially complete.

The solvents for the cyclization are aromatic hydrocarbon solvents such as benzene, toluene or xylenes; ethers such as diethyl ether, tetrahydrofuran, or 1,4-dioxane; chlorinated hydrocarbons such as methylene chloride, chloroform, carbon tetrachloride, dichloroethane, or chlorobenzene; amides such as dimethylformamide and dimethylacetamide; and other solvents such as hexamethylphosphoramide. Tetrahydrofuran is the preferred solvent. It is also desirable, but not essential, to dry and deoxygenate the solvent before use in the process.

While Reaction 7 in the above Scheme depicts the use of diethyl azodicarboxylate, the dimethyl and di(isopropyl)azodicarboxylate analogs can also be used in the reaction.

The chiral 1-(trifluoroacetyl)diazolidine obtained from Reaction 7 is deacylated with dilute sodium hydroxide solution. The deacylation is represented as Reaction 8 in the Scheme. The deacylation entails generally suspending the chiral 1-(trifluoroacetyl)diazolidine in water and adding at least two equivalents of a dilute aqueous solution of either sodium hydroxide or potassium hydroxide. For instance, a two-fold excess of 1M sodium hydroxide solution can be used. It is preferred to have the initial pH of the solution from between about 11 to about 12. The resultant solution can be stirred from about 10 minutes to about 3 hours at a temperature from about 10° C. to about 25° C. When the reaction is substantially complete the reaction solution is neutralized by the addition of dilute acid, such as 1N hydrochloric acid.

The optimal reaction time for the deacylation can be determined by monitoring the progress of the reaction with conventional chromatographic methods (such as thin layer chromatography, high performance liquid chromatography, or column chromatography), or spectroscopic methods, (such as infrared spectroscopy, nuclear magnetic resonance spectrometry and mass spectrometry) or a combination of both methods. A preferred reaction time is from between about 30 minutes to about 1.5 hours.

The synthesis of the above diazolidine starting materials are further described by L. N. Jungheim and R. E. Holmes, U.S. patent application Ser. No. 862,917, filed this even date, herein incorporated by reference, which application is in turn a continuation-in-part of L.-N. Jungheim, U.S. Patent Application Ser. No. 728,734, filed Apr. 30, 1985, herein incorporated by reference.

The bromoacetyl and chloroacetyl starting materials in Scheme 1 are made by methods known in the art and/or are commercially available.

III. Description of the Anitmicrobial Properties of the 7-Substituted Bicyclic Pyrazolidinones The compounds of Formula I are intermediates to the bicyclic pyrazolidinones (depicted in Scheme 2). The bicyclic pyrazolidinone antimicrobial compounds inhibit the growth of certain organisms pathogenic to man and animals. The preferred bicyclic pyrazolidinone antimicrobial compounds are compounds wherein the various amino, hydroxy and/or carboxy protecting groups have been removed and either $R_2$ or $R_3$ is an acyl group derived from a $C_1$ to $C_{30}$ carboxylic acid and the other is hydrogen. The antimicrobial activity can be demonstrated in vitro using standard tube-dilution techniques. These in vitro tests demonstrate that, in general, the 7-(S) isomers have better antimicrobial activity than either the corresponding 7-(R) isomers or a mixture of the two isomers. Representative pathogens which are sensitive to the antimicrobial compounds include *Staphylococcus aureus* X1.1, *Streptococcus pyogenes* C203, *Streptococcus pneumoniae* Park, *Hemophilus influenzae* 76 (ampicillin resistant), *Escherichia coli* N10, *Escherichia coli* EC14, *Escherichia coli* TEM (β-lactamase producer), *Klebsiella pneumoniae* X26, *Klebsiella pneumoniae* KAE (β-lactamase producer), *Klebsiella pneumoniae* X68, *Enterobacter* aerogenes C32, *Enterobacter aerogenes* EB17, *Enterobacter cloacae* EB5 (non-β-lactamase producer), *Salmonella typhi* X514, *Salmonella typhi* B35, *Serratia marcescens* X99, *Serratia marcescens* SE3, *Proteus morganii* PR51, *Proteus inconstans* PR33, *Proteus rettgeri* C24, *Citrobacter freundii* CF17, and the like.

The antimicrobial compounds that the compounds of this invention are intermediates to are useful for the therapeutic or prophylactic treatment of infections in warm-blooded animals caused by gram-positive, gram-negative, and acid-fast bacteria.

The antimicrobial compounds can be administered orally, parenterally (e.g. intravenously, intramuscularly or subcutaneously) or as a topical ointment or solution in treating bacterial infections of warm-blooded animals.

The bicyclic pyrazolidinone antimicrobial compounds can be formulated into pharmaceutical compositions. In particular, these pharmaceutical compositions are useful for the control of gram-positive and gram-negative bacterial infections and comprise a suitable vehicle and a therapeutically effective amount of the bicyclic pyrazolidinone antimicrobial compounds.

With regard to compositions for oral administration (such as tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as croscarmellose sodium, microcrystalline cellulose, corn starch, sodium starch glycolate, alginic acid and mutable wetting agents such as sodium lauryl sulfate; and lubricants such as magnesium stearate and other metallic stearates, stearic acid, silicone fluid, talc, waxes oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

The pharmaceutical compositions may also be in the form of oral liquid preparations, which may be either (a) aqueous or oily suspensions, solutions, emulsions or syrups; or (b) a dry powder to be reconstituted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol or ethyl alcohol; and preservatives such as methyl or propyl p-hydroxybenzoates or sorbic acid.

The pharmaceutical composition can also be for intravenous (IV) use. Specifically, a water soluble form of the antimicrobial compound can be dissolved in one of the commonly used intravenous fluids and administered by infusion. When used in conjunction with compositions for IV use, the term "suitable vehicle" means such fluids as physiological saline, Ringer's solution or 5% dextrose solution.

For intramuscular preparations a sterile formulation of a suitable salt form of the antimicrobial compound (for example, the hydrochloride salt or sodium salt) can be formulated with a "suitable vehicle". Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

Veterinary pharmaceutical compositions of the antimicrobial compounds may be administered in the feed or the drinking water of farm animals. Alternatively, the compounds can be formulated as intramammary preparations with "suitable vehicles" such as long- or quick-release bases.

The bicyclic pyrazolidinone antimicrobial compounds can also be formulated in unit dosage form in sterile vials, sterile plastic pouches containing a port with a septum, or sterile, hermetically sealed ampoules. The antimicrobial compound (or the corresponding pharmaceutically-acceptable salt) may be a dry powder or in crystalline or lyophylized form. The amount of the antimicrobial compound per unit dosage may vary from about 250 milligrams to about 10 grams.

A "therapeutically effective amount" of the bicyclic pyrazolidinone antimicrobial compounds is from approximately 2.5 mg to about 50 mg of compound per kilogram of body weight. This amount generally totals from about 1 gram to about 12 grams per day for an adult human.

A method for treating or controlling infectious diseases caused by gram-positive and gram-negative organisms in warm-blooded animals comprises administering to the infected host a therapeutically effective amount of the bicyclic pyrazolidinone antimicrobial compounds. A typical daily dose for an adult human in this method is from about 0.5 grams to about 12 grams.

In practicing this method, the antimicrobial compound can be administered in a single daily dose or in multiple doses per day. The treatment regime may require administration over extended periods of time, for example, for several days or for from two to three weeks. The amount administered per dose or the total amount administered will depend on such factors as the nature and severity of the infection, the age and general health of the patient, and the tolerance to the bicyclic pyrazolidinone antimicrobial compounds of both patient and the microorganism or microorganisms involved in the infection.

The following Examples are provided to further illustrate the invention. It is not intended that the invention be limited in scope by reason of any of the following Preparations or Examples.

In the following Preparations and Examples, the terms melting point, nuclear magnetic resonance spectra, electron impact mass spectra, field desorption mass spectra, infrared spectra, ultraviolet spectra, elemental analysis, high performance liquid chromatography, and thin layer chromatography are abbreviated m.p., n.m.r., m.s., f.d.m.s., i.r., u.v., anal., HPLC, and TLC, respectively. In addition, the adsorption maxima listed for the i.r. spectra are only those of interest and not all of the maxima observed.

The abbreviations THF and DMF stand for tetrahydrofuran and dimethylformamide, respectively.

In conjunction with the n.m.r. spectra, the following abbreviations are used: "s" is singlet, "d" is doublet, "dd" is doublet of doublets, "t" is triplet, "q" is quartet, "m" is multiplet, and "br.s" and "br.m" are broad singlet and multiplet, respectively. "J" indicates the coupling constant in Hertz. "DMSO-d$_6$" is dimethyl sulfoxide where all protons have been replaced with deuterium.

The n.m.r. spectra were obtained on a Varian Associates EM-390 90 MHz or T-60 60 MHz instrument, on a Jeol FX-90Q 90 MHz instrument, on a Brüker Corp. 270 MHz instrument or on a General Electric QE-300 300 MHz instrument. The chemical shifts are expressed in δ values (parts per million downfield from tetramethylsilane). The field desorption mass spectra were taken on a Varian-MAT 731 Spectrometer using carbon dendrite emitters. Election Impact Mass Spectra were obtained on a CEC 21-110 instrument from Consolidated Electrodynamics Corporation. Infrared spectra were obtained on a Perkin-Elmer 281 instrument. Ultraviolet Spectra were obtained on a Cary 118 instrument. Specific rotations were obtained on a Perkin-Elmer Q-41 instrument. Thin layer chromatography was carried out on E. Merck silica gel plates. Melting points are uncorrected.

EXPERIMENTAL SECTION

Preparation 1

Methyl 3-(p-Toluenesulfonate)-2-(S)-(t-Butoxycarbonylamino)Propionate

Methyl (3-hydroxy)-2-(S)-(t-butoxycarbonylamino)-propionate (58 g, 196 mmol), dry methylene chloride (150 ml), p-toluenesulfonyl chloride (43.35 g, 227.4 mmol), 4-(dimethylamino)pyridine (2.4 g, 19.6 mmol) and pyridine (30 ml, 371 mmol) were combined and stirred at room temperature overnight. The reaction solution was concentrated in vacuo to a pale yellow oil. The oil was stored in vacuo overnight, then the white solid that formed was isolated to give 75.33 g of crude product. The product was triturated in petroleum ether (approximately 200 ml) to yield methyl 3-(p-toluenesulfonate)-2-(S)-(t-butoxycarbonylamino)propionate:

n.m.r.: (CDCl$_3$, 90 MHz): δ 7.72, 7.31 (2x dd, 4, aromatic protons), 5.26 (m, 1, nitrogen proton), 4.48 (m, 1, C-2 proton), 4.32 (m, 2, C-3 protons), 3.68 (s, 3, methyl protons of methyl ester), 2.44 (s, 3, methyl protons of toluene moiety), 1.40 (s, 9, protons of t-butyl moiety); i.r. (CHCl$_3$) 3435, 3019, 1753, 1711, 1502, 1369, 1351, 1250, 1215, 1190, 1177 cm$_{-1}$; m.s.: 279, 210, 172, 91, 41;

Anal. Calcd. for C$_{16}$H$_{23}$NO$_7$S: Theory: C, 51.19; H, 6.71; N, 3.73; S, 8.54. Found: C, 51.05; H, 6.50; N, 3.63; S, 8.13.

Preparation 2

4-(R,S)-(t-Butoxycarbonylamino)-3-Oxo-1,2-Diazolidine

Under a nitrogen atmosphere, dry methylene chloride (50 ml) was cooled in an ice bath and anhydrous hydrazine (97%, 11.0 g, 333 mmole) was added. The ice bath was removed and the solution was stirred until it warmed to room temperature. At this time a solution of methyl 3-(p-toluenesulfonate)-2-(S)-(t-butoxycarbonylamino)propionate (20.0 g, 53.6 mmole) in dry methylene chloride (50 ml) was gradually added. The reaction solution was stirred under nitrogen at room temperature for 5 hours. The solution was then concentrated under reduced pressure and the concentrate was taken up in saturated aqueous sodium bicarbonate solution. The aqueous solution was continuously extracted for 14 hours with methylene chloride (700 ml). The methylene chloride solution was dried over sodium sulfate, filtered and concentrated under reduced pressure to yield approximately 5.15 g, 48% of 4-(R,S)-(t-butoxycarbonylamino)3-oxo-1,2-diazolidine: n.m.r. (CDCl$_3$, 90 MHz): δ 7.04 (m, 1), 5.12 (m, 1), 4.28 (m, 1, C-4 proton), 3.94 (m, 1, C-5 proton), 3.20 (m, 1, C-5 proton), 1.45 (s, 9, t-butyl protons); i.r. (CHCl$_3$) 3430, 3250, 3019, 2983, 1702, 1545, 1503, 1370, 1297, 1241, 1215, 1165 cm$^{-1}$; f.d.m.s.: M+=201;

Anal. Calcd. for C$_8$H$_{15}$N$_3$O$_3$: Theory: C, 47.75; H, 7.51; N, 20.88. Found: C, 47.80; H, 7.56; N, 20.61.

Preparation 3

4-(R,S)-(t-Butoxycarbonylamino)-3-Oxo-1,2-Diazolidine p-Toluenesulfonate Salt 4-(R,S)-(t-Butoxycarbonylamino)-3-oxo-1,2-diazolidine (1.7 g, 8.45 mmol) was slurried in methylene chloride (50 ml). p-Toluenesulfonic acid hydrate (1.6 g, 8.45 mmol) was added to the slurry. After 20 minutes the resultant solid material was collected then dried in vacuo for approximately 48 hours to yield 2.95 g of colorless 4-(R,S)-(t-butoxycarbonylamino)-3-oxo-1,2-diazolidine p-toluenesulfonate salt: n.m.r. (90 MHz, DMSO-d$_6$):δ 7.5 (d, 2, J=8), 7.1 (d, 2, J=8), 4.32 (m, 1), 3.9 (m, 1), 3.4 (m, 1) 2.3 (s, 3), 1.4 (s, 9); i.r. (KBr): 1742, 1704, 1537 cm$^{-1}$.

EXAMPLE 1

4-(R,S)-(t-Butoxycarbonylamino)-3-Oxo-1-(1'-(Thien-2"-yl) 1'-Oxoeth-2'-yl)-1,2-Diazolidine A DMF solution (150 ml) of 4-(R,S)-(t-butoxycarbonylamino)-3-oxo-1,2-diazolidine (12.06 g, 60 mmol) and sodium hydride (2.4 g, 60 mmol, 60% dispersion in mineral oil) were combined and the resultant mixture was stirred at room temperature for one hour then cooled to 0° C. A DMF solution (50 ml) of 2-(bromoacetyl)thiophene (12.9 g, 63 mmol) was added over a period of 15 minutes and the resultant mixture was stirred at 0° C. for approximately two to three hours, then stirred at room temperature for 18 hours. The reaction mixture was diluted with xylene (400 ml) and the solvents were removed in vacuo. The residue was dissolved in chloroform (400 ml) and water (200 ml). The chloroform layer was separated and the aqueous layer was extracted with chloroform (2×,200 ml). The chloroform layers were combined and washed with brine (3×,200 ml), dried over sodium sulfate, filtered and concentrated in vacuo to yield a red oil (26 g). The oil was chromatographed by preparatory-scale high performance liquid chromatography on a silica gel column eluted with a gradient of 1:1 toluene:ethyl acetate to 100% ethyl acetate to yield approximately 10 g of a yellow foam. The foam was recrystallized from diethyl ether to yield 5.53 g of a solid. The solid was slurried in diethyl ether, filtered, and the collected solid was washed with diethyl ether to yield 4.46 g of 4-(R,S)-(t-butoxy-carbonylamino-3-oxo-1-[1'-(thien-2''-yl)-1'-oxoeth-2'-yl]-1,2-diazolidine: n.m.r. (270 MHz, DMSO-$d_6$) δ 9.66 (s,1), 8.06 (m, 2), 7.27 (d, 1), 7.14 (d, 1), 4.6 (m, 1), 4.28 (dd, 2), 3.5 (t, 1), 3.11 (t, 1), 1.37 (9); i.r. (KBr): 1719, 1685, 1657 cm$^{-1}$; f.d.m.s. (m/e): M+=325.

Preparation 4

4-(R,S)-(t-Butoxycarbonylamino)-3-Oxo-2-(p-Nitrobenzyl Oxaloyl)-1-[1'-(Thien-2''-yl)-'-Oxoeth-2'yl]-1,2-Diazolidine A methylene chloride solution (20 ml) of 4-(R,S)-(t-butoxycarbonylamino)-3-oxo-1-(1'-(thien-2''-yl)-1'-oxoeth-2'-yl]-1,2-diazolidine (1.625 g, 5 mmol) was combined with di(iso-propyl)ethylamine (0.645 g, 5 mmol) and the resultant mixture was cooled to 10° C. A methylene chloride solution (20 ml) of p-nitrobenzyl oxalate acid chloride (1.217 g, 5 mmol) was added over a period of 20 minutes and the resulting mixture was stirred at 10°-15° C. for 4.5 hours then refrigerated overnight. The cold methylene chloride solution was washed with water (50 ml), brine (2×, 50 ml), dried over sodium sulfate, filtered and evaporated in vacuo. The residue was dissolved in chloroform (70 ml, ethanol-free) and used in the next step.

Preparation 5

2-(p-Nitrobenzyl Carboxylate)-3-(Thien-2-yl)-7-(R,S)-(t-Butoxycarbonylamino)-8-Oxo-1,5-Diazabicyclo [3.3.0]Octa-2-ene A chloroform solution (70 ml) of 4-(R,S)-(t-butoxycarbamylamino)-3-oxo-2-(p-nitrobenzyl oxaloyl)-1-[1'-(thien-2''-yl)-1'-oxoeth-2'-yl]-1,2-diazolidine (approximatley 5 mmol) taken from Preparation 4 above was combined with triethylphosphite (8.3 g, 50 mmol) and the mixture was heated to reflux for 24 hours and evaporated to dryness in vacuo. The residue was dissolved in ethyl acetate (300 ml) and the solution was washed with saturated aqueous sodium bicarbonate solution (2×, 100 ml), brine (2×, 100 ml), dried over sodium sulfate, filtered then evaporated in vacuo. Xylene (300 ml) was added to the residue then removed in vacuo. The resultant yellow oil was flash chromatographed over silica gel (100 g) eluted with 4:1 toluene, ethyl acetate to yield 0.643 mg of a yellow solid. The solid was recrystallized from ethyl acetate/hexanes to yield 0.471 g of 2-(p-nitrobenzyl carboxylate)-3-(thien-2-yl))-7-(R,S)-(t-butoxy carbonylamino)-8-oxo-1,5-diazobicyclo[3.3.0]octa-2-ene: n.m.r. (270 MHz, DMSO-$d_6$): δ 8.23 (d, 2), 7.78 (d, 1), 7.73 (d, 2), 7.45 (d, 1), 7.38 (d, 1, J=8.5), 7.16 (m, 1), 5.48 (q, 2), 4.72 (m, 1), 4.64 (d, 1, J=12), 4.12 (d, 1, J=12), 3.85 (t, 1), 2.98 (t, 1), 1.40, 1.36 (s, 9); i.r. (KBr): 1719, 1679 cm$^{-1}$; m.p. 186°-188° C.; u.v. (ethanol): $\lambda_{max}$=370 ($\epsilon_{max}$=13,059), 264 ($\epsilon_{max}$=18,327); f.d. m.s. (m/e): M+=500.

Preparation 6

2-(p-Nitrobenzyl Carboxylate)-3-(Thien-2-yl)-7-(R,S)-(Amino)-8-Oxo1,5-Diazobicyclo[3.3.0]Octa-2-ene 2-(p-(Nitrobenzyl carboxylate)-3-thien-2-yl) 7-(R,S)-(t-butoxycarbonylamino)-8-oxo-1,5-diazobicyclo [3.3.0]octa-2-ene (1.0 g, 2 mmol) was combined with trifluoroacetic acid (100 g, 61 ml) and the resultant solution was stirred for three minutes then evaporated in vacuo. Ethyl acetate (250 ml) and water (100 ml) were added to the residue and the resultant mixture was cooled to 0° C. The pH of the solution was adjusted to approximately 8.8 with aqueous saturated sodium bicarbonate solution. The aqueous layer was separated and extracted with ethyl acetate (2×, 125 ml). The ethyl acetate layers were combined, washed with brine (2×, 125 ml); dried over sodium sulfate, filtered and evaporated in vacuo to give 0.797 g of 2-(p-nitrobnezyl carboxylate)-3-(thien-2-yl)-7-(R,S)-(amino)-8-oxo-1,5-diazobicyclo [3.3.0]octa-2-ene. The solid was dissolved in acetonitrile (60 ml) and used in the next step.

Preparation 7

2-(p-Nitrobenzyl Carboxylate)-3-(Thien-2-yl)-7-(R,S)-[2-(2-Aminothiazol-4-yl)-2-(Z)-Methoxyiminoacetamido]-8-Oxo-1,5-Diazobicyclo[3.3.0]Octa-2-ene An acetonitrile solution (60 ml).of 2-(p-nitrobenzyl carboxylate)-3-(thien-2-yl)-7-(R,S)-(amino)-8-oxo-1,5-diazobicyclo[3.3.0]octa-2-ene (0.797 was combined with diisopropylethylamine (0.2967 g, 2.3 mmol, 0.4 ml) and (1-hydroxy N-benzotriazolyl) 2-(2'- aminothiazol-4'-yl)-2-(Z)-methoximinoacetate (0.6678 g, 2.1 mmol) and the resultant mixture was stirred at room temperature for 20 hours and then evaporated in vacuo. The residue was dissolved in a mixture of ethyl acetate (600 ml) and aqueous saturated sodium bicarbonate solution (100 ml). The ethyl acetate layer was separated then extracted with aqueous saturated sodium bicarbonate solution (100 ml), brine (2×, 150 ml), dried over sodium sulfate, filtered and evaporated to dryness in vacuo to yield a yellow solid. The solid was recrystallized from ethyl acetate to yield 0.57 g of 2-(p-nitrobenzyl carboxylate)-3-(thien-2-yl)-7-(R,S)-[2-(2-amino- thiazol-4-yl)-2-(Z)-methoxyimino-acetamido]-8-oxo-1,5diazobicyclo[3.3.0]octa-2-ene: n.m.r. (360 MHz, DMSO-$d_6$): δ 9.14 (d, 1, J=8.5), 8.23 (d, 2), 7.80 (d, 1), 7.75 (d, 2), 7.48 (d, 1), 7.2 (br. s, 2), 7.17 (m, 1), 7.00 (s, 1), 5.50 (q, 2), 5.08 (m, 1), 4.65 (d, 1, J=12), 4.22 (d, 1, J=12), 3.94 (t, 1), 3.83 (s, 3), 3.14 (t, 1); i.r. (KBr): 1709 cm$^{-1}$; u.v. (ethanol): $\lambda_{max}$=370 ($\epsilon_{max}$=12,692), 260 ($\epsilon_{max}$=25,332); f.d. m.s. (m/e): M+=584.

Preparation 8

2-(Carboxylic Acid)-3-(Thien-2-yl)-7-(R,S)-[2-(2-Aminothiazol-4-yl)-2-(Z)-Methoxyiminoacetamido]-8-Oxo-1,5-Diazabicyclo[3.3.0]Octa-2-ene 2-(p-Nitrobenzyl carboxylate)-3-(thien-2-yl)-7-(R,S)-[2-(2-aminothiazol-4-yl)-2-(Z)-methoxyiminoacetamido]-8-oxo-1,5-diazobicyclo[3.3.0]octa-2-ene (0.618 g, 1.048 mmol) was electrolytically reduced under the following conditions:

The electrochemical cell had the cathode and the anode compartments separated by a fritted glass disc. The cathode was a mercury pool with 14 cm$^2$ surface area immersed in a catholyte of 9:1 DMF:12N sulfuric acid (total volume of 40 ml). The cathode compartment was fitted with a deaerating frit and an SCE reference electrode. Both compartments were purged with argon before the electrolysis. The anode was a platinum wire ring and the anolyte was the same as the catholyte. The temperature of the cell was maintained at 25° C. for the electrolysis. A constant potential of −0.5 V was maintained and the progress of the reduction was monitored by HPLC. The reduction was stopped at approximately 91% completion (370 q).

The catholyte was chromatographed by preparatory-scale high performance liquid chromatography on a $C_{18}$ reverse phase column eluted with a gradient of 0–15% acetonitrile/1% acetic acid/water. The product-containing fractions were combined and lyophilized to yield 88.7 mg of 2-(carboxylic acid)-3-(thien-2-yl)-7-(R,S)-[2-(2-aminothiazol-4-yl)-2-(Z)-methoxyimino]acetamido-8-oxo-1,5-diazabicyclo[3.3.0]octa-2-ene: n.m.r.: δ 9.12 (d, 1, J=9), 7.7 (d, 1), 7.37 (d, 1), 7.22 (br. s, 2), 7.13 (m, 1), 7.06 (s, 1), 5.04 (t, 1), 4.54 (d, 1, J=12), 4.09 (d, 2, J=12), 3.9 (t, 1), 3.86 (s, 3), 3.07 (t, 1); i.r. (KBr): 1685, 1676, 1628 cm$^{-1}$; u.v. (ethanol): $\lambda_{max}=344$ ($\epsilon_{max}=15,727$), 292 $\epsilon_{max}10,516$), 236 ($\epsilon_{max}=18,645$) f.d.m.s. (m/e): M$^+=448$.

Preparation 9

N-(t-Butoxycaronyl) (L)-Serine Trifluoroacetyl Acyl Hydrazide

N-(t-Butoxycarbonyl) (L)-serine acyl hydrazide (32.85 g, 150 mmol) was suspended in ethanol (400 ml). Ethylthio trifluorothioacetate (30 ml, 37.02 g, 234.3 mmol) was added to the suspension and the resultant mixture was stirred at room temperature for 65 hours. The solvent was removed in vacuo and the residue was dissolved in diethyl ether (160 ml). A seed crystal was added to the diethyl ether solution and the resultant crystals were collected by filtration (approx. 27 g). The filtrate was evaporated in vacuo and diethyl ether (50 ml) was added to the residue. The solids that formed on standing were removed by filtration to yield approximately 16.5 g of additional product. The two batches of solids collected by filtration were combined and recrystallized from diethyl ether (3 liters). After effecting solution, the solution was reduced to approximately 450 ml to yield (after a second crop) 41.04 g, 87% yield of N-(t-butoxycarbonyl) (L)-serine trifluoroacetyl acyl hydrazide: n.m.r. (300 MHz, DMSO-d$_6$): δ 11.5 (br. s, 1), 10.33 (s, 1), 6.84 (d, 1, J=9), 4.9 (t, 1, J=7, (OH), 4.1 (m, 1), 3.59 (br. m, 2), 1.4 (s, 9); specific rotation: $[\alpha]_D^{25}=-25.87°$ (10.05 mg/ml, methanol); m.p.: 143°–144° C. (first crop), 142°–144° C. (second crop).

Anal. Calcd for $C_{10}H_{16}N_3O_5F_3$: Theory: C, 38.10; H, 5.12; N, 13.33; Found: C, 38.34; H, 4.89; N, 13.16.

Preparation 10

4-(S)-(t-Butoxycarbonylamino)-1-(Trifluoroacetyl)-3-Oxo-1,2-Diazolidine

N-(t-Butoxycarbonyl) (L)-serine trifluoroacetyl acyl hydrazide (3.78 g, 12 mmol) and triphenylphosphine (3.46 g, 13.2 mmol) were dissolved in THF (50 ml). To the solution was added a THF solution (10 ml) of 95% diethyl azodicarboxylate (2.42 g, 2.19 ml, 13.2 mmol). The resultant mixture was stirred at room temperature for six hours and then the solvent was removed in vacuo. The residue was dissolved in ethyl acetate (100 ml) and then the solution was washed with aqueous sodium bicarbonate solution (33 ml, 3×). The sodium bicarbonate extracts were combined, aqueous saturated brine solution (70 ml) was added and the resultant mixture was extracted with ethyl acetate (120 ml, 3×). The sodium bicarbonate solution was then layered with additional ethyl acetate (200 ml) and 1N hydrochloric acid (approx. 80 ml) was added until the sodium bicarbonate solution had a pH of 2.5. The ethyl acetate layer was separated and the aqueous layer was extracted with additional ethyl acetate (4×,125 ml). The ethyl acetate extracts were combined, washed with saturated aqueous brine (125 ml, 2×), dried over sodium sulfate, filtered, and taken to dryness in vacuo. The resultant residue was dissolved in acetonitrile (100 ml) then the acetonitrile was removed in vacuo. Treatment of the residue with acetonitrile was repeated to yield 3.06 g, 96% yield of 4-(S)-(t-butoxycarbonylamino)-1-(trifluoroacetyl)-3-oxo-1,2-diazolidine: n.m.r. (30 MHz: CDCl$_3$) δ 5.25 (d, 1, J=6), 4.81 (t, 1), 4.6 (m, 1), 4.06 (t, 1), 1.46 (s, 9); i.r. (CHCl$_3$): 1722, 1682, 1518 cm$^{-1}$; f.d.m.s. (m/e): M$^+=297$; specific rotation: $[\alpha]_D^{25}=-88.14°$ (10.03 mg/ml in methanol);

Anal. Calcd for $C_{10}H_{14}N_3O_4F_3$: Theory: C, 40.41; H, 4.75; N, 14.14; Found: C, 40.58; H, 5.01; N, 13.92.

Preparation 11

4-(S)-(t-Butoxycarbonylamino)-3-Oxo-1,2-Diazolidine 4-(S)-(t-butoxycarbonylamino)-1-(trifluoroacetyl)3-oxo-1,2-diazolidine (2.97 g, 10 mmol) was suspended in water (30 ml), 1N sodium hydroxide solution (20 ml, 0.8 g, 20 mmol) was added to raise the pH of the solution to 12.2 and the resultant mixture was stirred for one hour at room temperature. The pH of the mixture was adjusted to 7.2 by the addition of 1N hydrochloric acid (10 ml). Sodium chloride (13 g) was added to the solution and the mixture was extracted with chloroform (50 ml, 8×). The chloroform extracts were combined, washed with saturated aqueous sodium chloride solution (75 ml), dried over sodium sulfate, filtered, and evaporated to dryness in vacuo. Diethyl ether (100 ml) was added to the residue and then the ether was removed in vacuo to yield 0.798 g of a white solid of 4-(S)-(t-butoxycarbonylamino)-3-oxo-1,2-diazolidine: n.m.r. (300 MHz, DMSO-d$_6$) δ 9.23 (s, 1), 7.04 (d, 1, J=9), 5.24 (br. s, 1,), 4.24 (m, 1), 3.41 (t, 1), 2.88 (t, 1), 1.38 (s, 9); specific rotation: $[\alpha]_D^{25}=-74.16°$ (10.06 mg/ml in methanol); (the compound was dried overnight at 80° C. before analysis):

Anal. Calcd for $C_8H_{15}N_3O_3$: Theory: C, 47.75; H, 7.51; N, 20.88; Found: C, 47.75; H, 7.46; N, 20.62.

We claim:

1. A compound of the formula:

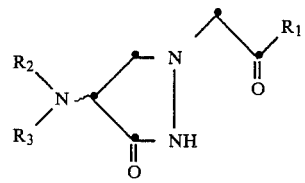

wherein:

$R_1$ is $C_1$ to $C_6$ alkyl, $C_1$ to $C_6$ substituted alkyl, perfluoro $C_2$ to $C_4$ alkyl, $C_7$ to $C_{12}$ arylalkyl, $C_7$ to $C_{12}$ substituted arylalkyl, phenyl, substituted phenyl, or a heterocyclic ring; a group of the formula

—CX$_3$ wherein X is fluoro, chloro, bromo or iodo; or a group of the formula

—S—R$_4$ wherein $R_4$ is $C_1$ to $C_6$ alkyl, $C_1$ to $C_6$ substituted alkyl, phenyl, substituted phenyl, $C_7$ to $C_{12}$ arylalkyl, $C_7$ to $C_{12}$ substituted arylalkyl or a heterocyclic ring;

$R_2$ and $R_3$ are:
(1) each hydrogen;
(2) taken together and form a phthalimido group; or
(3) different and are either hydrogen or an amino-protecting group;

or a pharmaceutically-acceptable salt thereof.

2. A compound of claim 1, wherein either $R_2$ or $R_3$ is hydrogen and the other is an amino-protecting group.

3. A compound of claim 2, wherein $R_1$ is a heterocyclic ring.

4. A compound of claim 3, wherein $R_1$ is 2-thienyl.

5. A compound of claim 4, wherein either $R_2$ or $R_3$ is hydrogen and the other is a t-butoxycarbonyl group.

6. A compound of claim 1 of the formula

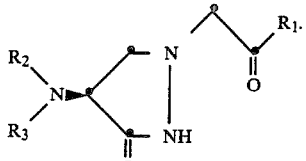

7. A compound of claim 6, wherein either $R_2$ or $R_3$ is hydrogen and the other is an amino-protecting group.

* * * * *